United States Patent [19]

Ingolia

[11] Patent Number: 4,559,302
[45] Date of Patent: Dec. 17, 1985

[54] DNA FOR DIRECTING TRANSCRIPTION AND EXPRESSION OF STRUCTURAL GENES

[75] Inventor: Thomas D. Ingolia, Indianapolis, Ind.

[73] Assignee: Eli Lilly and Company, Indianapolis, Ind.

[21] Appl. No.: 438,070

[22] Filed: Nov. 1, 1982

[51] Int. Cl.$^4$ .................. C12N 15/00; C12N 1/20; C12N 1/00; C12P 21/00; C12P 21/02; C07H 15/12

[52] U.S. Cl. .................. 435/172.3; 435/68; 435/70; 435/172.1; 435/317; 435/253; 935/27; 935/29; 935/56; 935/41; 536/27

[58] Field of Search ............. 435/68, 70, 172, 172.3, 435/317, 253; 536/27

[56] References Cited

U.S. PATENT DOCUMENTS 4,237,224 12/1980 Cohen et al. ................. 435/68
4,349,629 9/1982 Carey et al. ................ 435/172.3

OTHER PUBLICATIONS

Guarente, et al., Science vol. 209, 19 (Sep. 1980), pp. 1428–1430.
Sutcliff et al., in *Genetic Engineering*, Chakrabarty (ed.), CRC Press (1978), pp. 83–111.
Rao et al., Gene 7 (1979) 79–82.
Zwiebel et al., J. of Bacteriology, vol. 145, No. 1, pp. 654–656, Jan. 1981.
Davies and O'Connor, 1978, Antimicrobial Agents and Chemotherapy 14(1):69.
"Compilation and Analysis of *Escherichia coli* Promoter DNA Sequences", Diane K. Hawley and William R. McClure, *Nucleic Acids Research*, vol. 11, No. 8, pp. 2237–2255, (1983).
"Functional Expression of Cloned Yeast DNA in *Escherichia coli*: Specific Complementation of Argininosuccinate Lyase (argH) Mutations", Louise Clarke and John Carbon, *J. Mol. Biol.*, vol. 120, pp. 517–532, (1978).
"In Vitro Gene Fusions That Join an Enzymatically Active B-Galactosidase Segment to Amino-Terminal Fragments of Exogenous Proteins: *Escherichia coli* Plasmid Vectors for the Detection and Cloning of Translational Initiation Signals", Malcolm J. Casadaban, Joany Chou, and Stanley N. Cohen, *Journal of Bacteriology*, vol. 143, No. 2, pp. 971–980, (Aug. 1980).
"The Lactose Operon", Edited by J. R. Beckwith and D. Zipser, Cold Spring Harbor Laboratory, 1970.
A.T.C.C. Quarterly Newsletter, Apr. 1982, vol. 2, No. 4.

Primary Examiner—Thomas G. Wiseman
Assistant Examiner—Robin Teskin
Attorney, Agent, or Firm—Gerald V. Dahling; Arthur R. Whale

[57] ABSTRACT

The present invention relates to a novel transcriptional and translational activating sequence. The novel activating sequence can be either chemically synthesized or isolated on a 0.17 kb PstI-SacI restriction fragment from plasmid pKC203, a plasmid of *E. coli* JR225 (ATCC 31912). The activating sequence directs expression of the aminoglycoside acetyltransferase aac(3)IV and hygromycin phosphotransferase aph(4) genes present on plasmid pKC203. A series of expression vectors have been constructed in which the activating sequence directs the expression of beta-galactosidase or hygromycin phosphotransferase. These vectors can be readily modified and have been designed to facilitate the subsequent cloning and expression of any gene of research or commercial interest. The expression and cloning vectors have been transformed into *E. coli* and other host cells in which the activating sequence functions.

18 Claims, 6 Drawing Figures

Figure 1
Restriction Site Map of Plasmid pKC222

Restriction Site Map of Plasmid pKC222

Restriction Site Map of Plasmid pKC203**

Restriction Site Map of Plasmid pTI104 and pTI106

Apramycin (aac (3) IV)—Hygromycin B (aph (4)) Promoter,
Shine-Dalgarno Sequence and Translational-Start Triplet Synthesis Procedure for Fragment T₇

Construction Route for Apramycin (aac(3) IV)-Hygromycin B (aph (4)) Promoter, Shine-Dalgarno Sequence and Translational-Start Triplet

DNA FOR DIRECTING TRANSCRIPTION AND EXPRESSION OF STRUCTURAL GENES

The present invention is a novel DNA which is useful for directing transcription and expression of structural genes and which comprises a promoter and a Shine-Dalgarno sequence. The invention further comprises vectors and transformants containing the aforementioned DNA.

The present invention is related generally to U.S. patent application Ser. No. 362215 now abandoned, filed on Mar. 26, 1982. The aforementioned application discloses starting materials, including plasmid pKC222 and the hygromycin B and G418 resistance-conferring DNA segments therein, which are useful for constructing the present invention. However, the application does not disclose the present DNA or suggest its utility for directing transcription and expression of structural genes.

The development and exploitation of recombinant DNA technology has been limited by the general paucity of DNA sequences that direct gene transcription and expression. Although the lac (Roberts et al., 1979, Proc. Nat. Acad. Sci. USA 76:5596 and Guarente et al., 1980, Cell 20:543), trp (Hallewell and Emtage, 1980, Gene 9:27), Bacteriophage λPL (Remaut et al., 1981, Gene 15(1):81, Bernard et al., 1979, Gene 5:59 and Derom et al., 1982, Gene 17:45) and lpp (Zwiebel et al., 1981, J. Bacteriol. 145:654, Lee et al., 1981, J. Bacteriol. 146:861 and Natamura and Inouye, 1979, Cell 18:1109) promoter systems are known, few, if any, other DNA sequences are available for driving the expression of genes that code for functional polypeptides. The present invention provides novel DNA which is useful for expressing such genes in *E. coli* and also other host cells and therefore represents a significant advance in the technical art.

For purposes of the present invention as disclosed and claimed herein, the following terms are as defined below.

Recombinant DNA Cloning Vector—any autonomously replicating agent, including but not limited to plasmids, comprising a DNA molecule to which one or more additional DNA segments can or have been added.

Transformation—the introduction of DNA into a recipient host cell that changes the genotype and results in a change in the recipient cell.

Transformant—a recipient host cell that has undergone transformation.

Restriction Fragment—any linear DNA generated by the action of one or more restriction enzymes.

Apramycin Resistance Genotype—aac(3)IV.

Hygromycin B Resistance Genotype—aph(4).

Functional Polypeptide—a recoverable bioactive entirely heterologous polypeptide or precursor, a recoverable bioactive polypeptide comprising a heterologous polypeptide and a portion or whole of a homologous polypeptide, or a recoverable bioinactive fusion polypeptide comprising a heterologous polypeptide and a bio-inactivating homologous polypeptide which can be specifically cleaved.

Fused Gene Product—a recoverable heterologous polypeptide which is fused with a portion or whole of a homologous polypeptide.

Structural Gene—DNA that encodes a functional polypeptide but that lacks a promoter and Shine-Dalgarno sequence.

DETAILED DESCRIPTION OF THE INVENTION

Figure 1:
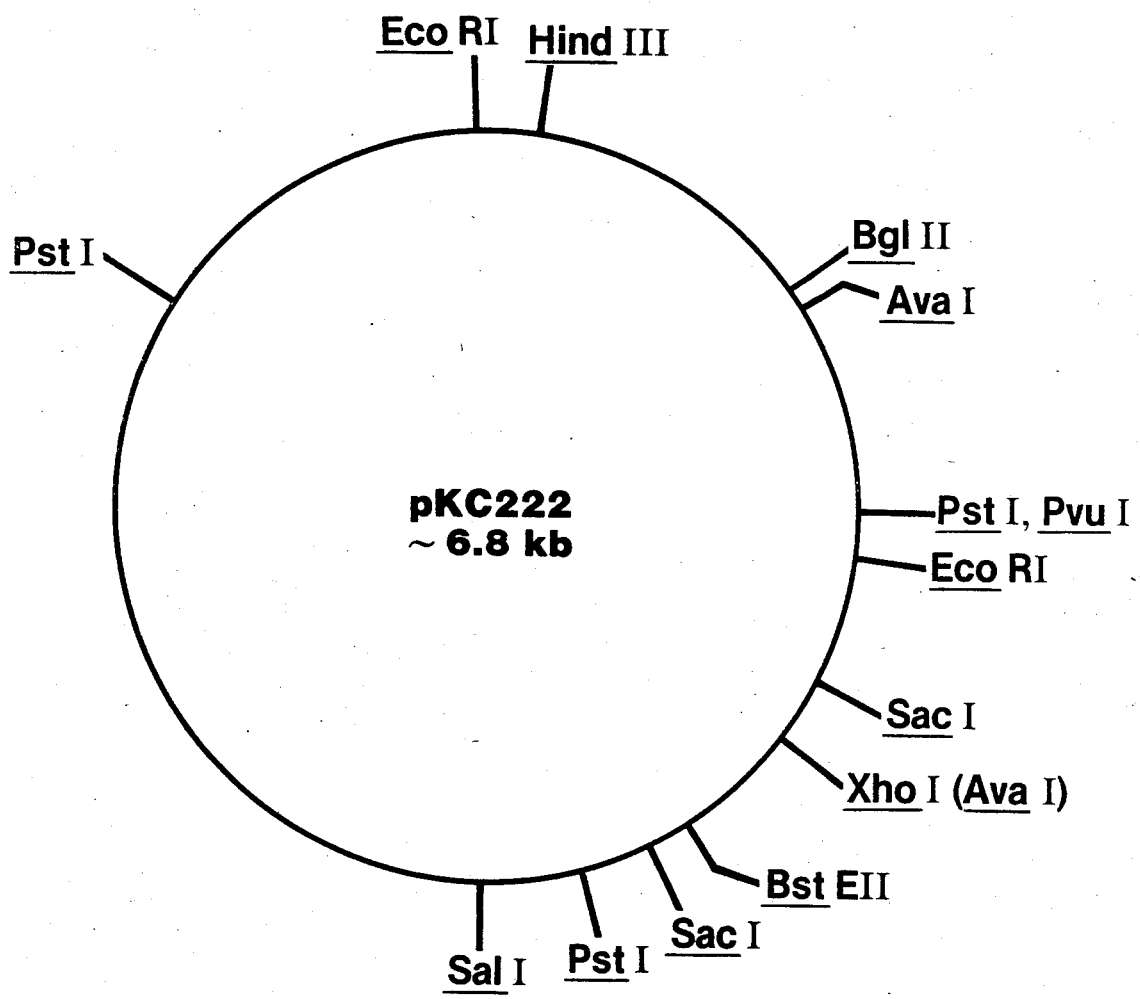

The present invention is novel DNA comprising the promoter, Shine-Dalgarno sequence and the translational-start triplet of the polycistronic apramycin (aac(3)IV) and hygromycin B (aph(4)) resistance genes. The invention further comprises both the aforementioned DNA ligated in translational reading phase with a gene that encodes a functional polypeptide and also recombinant DNA cloning vectors and transformants comprising the aforementioned DNA alone or in reading phase with said gene.

More particularly, the DNA of the present invention comprises the following deoxyribonucleotide sequence wherein
A is deoxyadenyl,
G is deoxyguanyl,
C is deoxycytosyl and
T is thymidyl:

```
5'-ATTTGCAACAGTGCCGTTGATCGTGCTATGA
   ||||||||||||||||||||||||||||||
3'-TAAACGTTGTCACGGCAACTAGCACGATACT

TCGACTGATGTCATCAGCGGTGGAGTGCAATG-3'
||||||||||||||||||||||||||||||||
AGCTGACTACAGTAGTCGCCACCTCACGTTAC-5'
                   Shine-     Met
                   Dalgarno
```

The present deoxyribonucleotide sequence can be conventionally synthesized by the modified phosphotriester method using fully protected trideoxyribonucleotide building blocks in substantial accordance with the procedures of Itakura et al., 1977, Science 198:1056 and Crea et al., 1978, Proc. Nat. Acad. Sci. USA 74:5765. Alternatively, the present invention can also be constructed by PstI and SacI digestion of plasmid pKC222. The resultant ~0.17 kb PstI-SacI fragment contains the above sequence and also additional deoxyribonucleotides at both termini. The additional deoxyribonucleotides at the 3' end of the coding strand code for the first 9 amino acids of the apramycin resistance-conferring polypeptide. Therefore, ligation in reading phase of a structural gene at the SacI site results in a DNA sequence that encodes a fused gene product comprising the first 10 (including the ATG encoded methionine) amino acids of the apramycin resistance-conferring polypeptide and the particular polypeptide encoded by the structural gene. Those skilled in the art will recognize that a similar ligation directly after the ATG translation-start triplet results in a sequence that encodes a polypeptide that contains a terminal methionine but that lacks other apramycin resistance-related amino acids. Therefore, a variety of fused gene products can be encoded depending upon where after the ATG start triplet a particular structural gene is ligated.

Direct expression of a gene product is also possible when the polypeptide encoded by the structural gene begins with methionine. In that case, the structural gene can be cleaved by a restriction enzyme and then reconstructed synthetically (Itakura et al., 1977 and Crea et al., 1978) so as to lack the ATG methionine-encoding start triplet. Alternatively, depending upon convenience and ease of construction, the modified gene may be entirely synthetic. In either case, the modified gene can be ligated in reading phase directly after the present ATG translational start triplet thus restoring the methionine-encoding triplet and thus allowing for direct expression of a desired product.

Plasmid pKC222, from which the DNA of the present invention can be obtained, is ~6.8 kb and is constructed by ligating the ~2.75 kb SalI-BglII fragment of plasmid pKC203 to the ~2.7 kb SalI-BglII fragment of plasmid pKC7. Plasmid pKC203 is ~15 kb and can be conventionally isolated from *E. coli* JR225, a strain deposited and made part of the stock culture collection of the American Type Culture Collection, Rockville, Md. The strain is available to the public as a preferred source and stock reservoir of plasmid pKC203 under the accession number ATCC 31912. Plasmid pKC7 is known in the art and can be constructed in accordance with the procedure disclosed in Rao and Rogers, 1979, Gene 7:79. A restriction site map of each of plasmids pKC222 and pKC203 is presented respectively in FIGS. 1 and 2 of the accompanying drawings.

Figure 3:
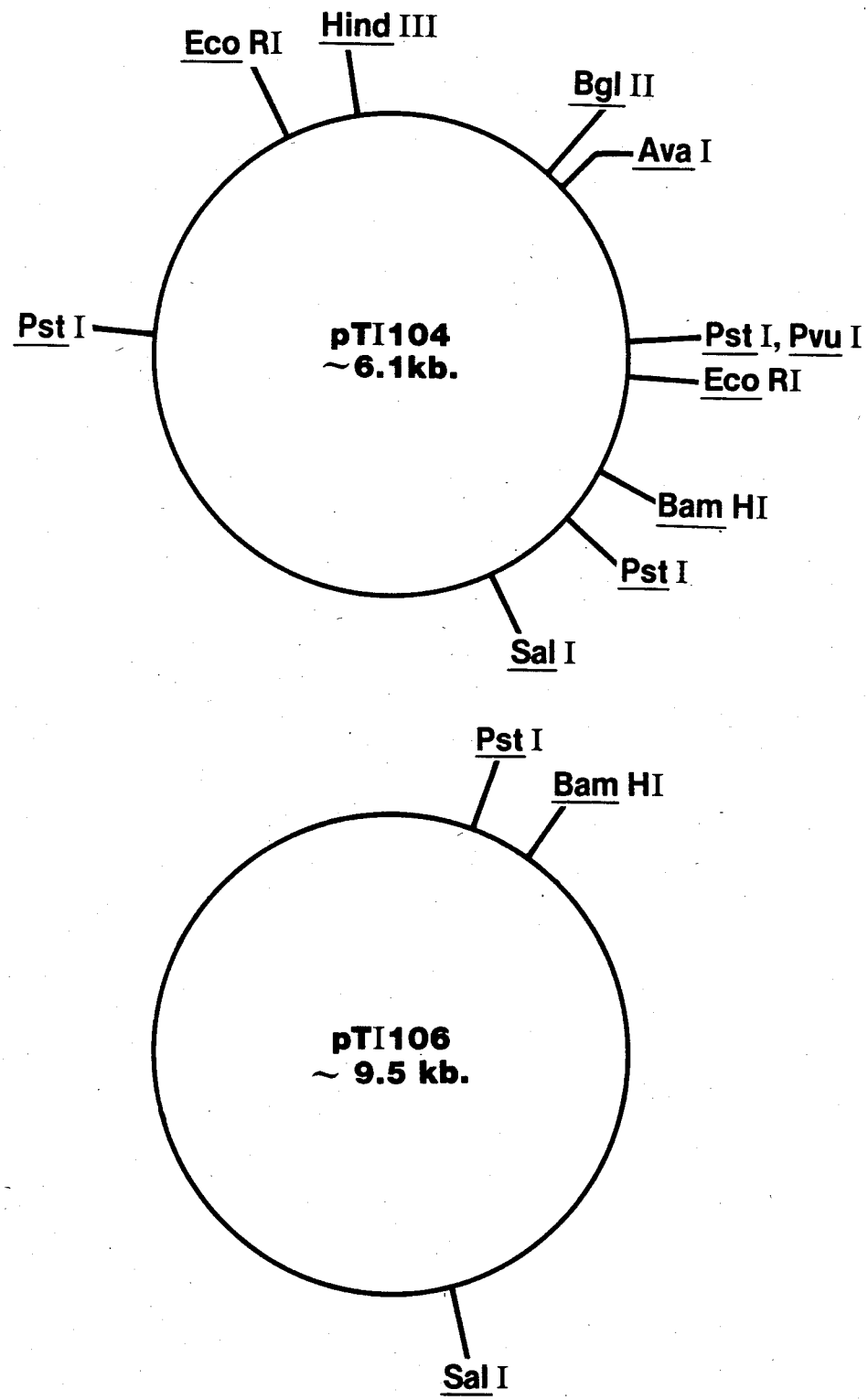

For convenience and ease of construction, the ~0.17 kb PstI-SacI fragment, which contains the present DNA sequence, was ligated to a fragment of the lacZ gene-containing plasmid pMC1403. Plasmid pMC1403 is ~9.9 kb and can be conventionally isolated from *E. coli* K12 BE904/pMC1403, a strain deposited and made part of the stock culture collection of the Northern Regional Research Laboratory, Peoria, Ill. The strain is available to the public as a preferred source and stock reservoir of plasmid pMC1403 under the accession number NRRL B-15213. The aforementioned ligation was carried out after the SacI site of the ~0.17 kb PstI-SacI fragment was changed to a BamHI site. This was done by SacI deletion of plasmid pKC222, including the resultant SacI 3' extensions, followed by the addition of 10-mer BamHI linkers to the flush ends. Ligation of the thus modified linear pKC222 DNA resulted in the derivative plasmid pTI104. Those skilled in the art will recognize that the DNA sequence of the present invention is contained in the ~0.17 kb PstI-BamHI fragment of plasmid pTI104. A restriction site map of plasmid pTI104 is presented in FIG. 3 of the accompanying drawings.

The usefulness of the present invention was exemplified by ligating the ~0.17 kb PstI-BamHI fragment of plasmid pTI104 to the ~9.3 kb PstI-BamHI fragment of plasmid pMC1403. The latter fragment comprises most of the lacZ gene (starting at amino acid 8), but does not contain a DNA sequence that directs transcription and expression of the gene. Since the BamHI site of plasmid pMC1403, which is located at the triplet for amino acid 8 of B-galactosidase, has the same translational reading frame as the ~0.17 kb PstI-BamHI fragment of pTI104, ligation of the aforementioned fragments results in a plasmid, illustrative of the present invention and designated herein as pTI106, that has the lacZ structural gene under the control of the present transcription and expression-directing DNA. Thus, when lacZ mutant *E. coli* K12 BE904 cells were transformed by illustrative plasmid pTI106, the lacZ gene was expressed and dark blue colonies were produced on X-G plates. Gene expression and the concomitant presence of B-galactosidase were further confirmed by in vitro assay, conclusively establishing the usefulness of the present DNA sequence for directing transcription and expression of structural genes. A restriction site map of plasmid pTI106 is presented in FIG. 3 of the accompanying drawings.

The present invention is particularly versatile and can be applied to the production of any polypeptide which can be encoded by a structural gene in a recombinant DNA cloning vector. A preferred recombinant DNA cloning vector is the plasmid although bacteriophage and other vectors can also be used and are apparent to those skilled in the art. In addition to the illustrative lacZ gene, other structural genes that can be used include genes that are naturally occurring, genes that are non-naturally occurring and genes which are in part naturally occurring and in part synthetic or non-naturally occurring. More particularly, the present DNA sequence can be used to promote and direct expression of structural genes coding for human pre-proinsulin, human proinsulin, human insulin A-chain, human insulin B-chain, non-human insulin, human growth hormone, non-human growth hormone, bovine growth hormone, human interferon, non-human interferon, viral antigen, urokinase, any peptide hormone, any enzyme or virtually any other polypeptide with research or commercial value.

The wealth of genetic and biochemical information about *E. coli* makes it a convenient host cell for purposes of the present invention. However, the invention is not limited to any one genus, species or strain but can be used with any organism where the present apramycin-hygromycin B promoter-Shine-Dalgarno sequence is functional. For example, the invention is applicable to prokaryotes, including but not limited to *E. coli, E. coli* K12, *E. coli* K12 HB101, Bacillus, Staphylococcus, Streptococcus, Actinomycetes, Streptomyces, Serratia and Pseudomonas; and fungi, including but not limited to Neurospora, Cephalosporium, Aspergillus, Penicillium and yeast.

The following examples further illustrate the invention disclosed herein. Both an explanation of and the actual procedures for constructing the invention are described where appropriate.

EXAMPLE 1

Construction of Plasmid pKC222 and *E. coli* K12 RR1/pKC222

A. Isolation of Plasmid DNA From *E. coli* JR225 and Construction of Plasmid pKC203

The bacterium *E. coli* JR225 (ATCC No. 31912) was cultured in TY broth (1% tryptone, 0.5% yeast extract, 0.5% sodium chloride, pH 7.4) with 100 μg./ml. of antibiotic hygromycin B according to conventional microbiological procedures. After 18 hours incubation, about 0.5 ml. of the culture was transferred to a 1.5 ml. Eppendorf tube and centrifuged for about 15 seconds. Unless otherwise indicated, all the manipulations were done at ambient temperature. The resultant supernatant was carefully removed with a fine-tip aspirator and the cell pellet was suspended in about 100 μl. of freshly prepared lysozyme solution which contained 2 μg./ml. lysozyme, 50 mM glucose, 10 mM CDTA (cyclohexane diaminetetracetate) and 25 mM Tris-HCl (pH 8). After incubation at 0° C. for 30 minutes, about 200 μl. of alkaline SDS (sodium dodecyl sulfate) solution (0.2N NaOH, 1% SDS) were added and the tube was gently vortexed and then maintained at 0° C. for 15 minutes. Next, about 15 μl. of 3M sodium acetate (prepared by dissolving 3 moles of sodium acetate in a minimum of water, adjusting the pH to 4.8 with glacial acetic acid and then adjusting the volume to 1 l.) were added and the contents of the tube were then mixed gently by inversion for a few seconds during which time a DNA clot formed.

The tube was maintained at 0° C. for 60 minutes and then centrifuged for 5 minutes to yield an almost clear supernatant. About 0.4 ml. of the supernatant were transferred to a second centrifuge tube to which 1 ml. of cold ethanol was added. After the tube was held at −20° C. for 30 minutes, the resultant precipitate was collected by centrifugation (2 minutes) and the supernatant was removed by aspiration. The thus collected pellet was dissolved in 100 μl. of 0.1M sodium acetate/0.5M Tris-HCl (pH 8) and was reprecipitated by the addition of 2 volumes of cold ethanol. After 10 minutes at 20° C., the precipitate was collected, as described above, by centrifugation and constituted the desired *E. coli* JR225 plasmid DNA.

B. Transformation of *E. coli* JR225 Plasmid DNA and Isolation of Plasmid pKC203

The *E. coli* JR225 plasmid DNA pellet was dissolved in about 100 μl. of 0.1M sodium acetate/0.05M Tris-HCl (pH 8) and precipitated with 2 volumes of cold ethanol. The resultant plasmid DNA was collected and dissolved in about 40 μl. of water or dilute buffer and then used to transform *E. coli* K12 BE827 in substantial accordance with the transformation method of Wensink, 1974, Cell 3:315. Bacterial strain *E. coli* K12 BE827 has been deposited and made part of the stock culture collection of the American Type Culture Collection, Rockville, Md., from which it is available to the public without restriction under the number ATCC 31911.

The resultant transformants were selected on TY agar (1% tryptone, 0.5% yeast extract, 0.5% sodium chloride, 1.5% agar, pH 7.4) containing 200 μg./ml. of antibiotic hygromycin B. Some of the transformants, as shown by agarose gel electrophoresis (Rao and Rogers, 1978, Gene 3:247) and other tests, contained both large and smaller (15 kb) plasmids and were resistant to both antibiotics ampicillin and hygromycin B. Other transformants contained only the smaller 15 kb plasmid and were resistant to antibiotics hygromycin B and G418 but were sensitive to ampicillin. Transformants of the latter type were plated on TY agar containing 0.1 mg./ml. of antibiotic hygromycin B and were cultured using standard microbiological techniques. The resultant cells were used, according to the procedure of Example 1A, to isolate the above described 15 kb hygromycin B and G418 resistance-conferring plasmid, hereinafter designated as plasmid pKC203. The presence of the antibiotic hygromycin B and G418 resistance genes on plasmid pKC203 was confirmed by subsequent transformation and selection analysis.

C. Construction of the ∼2.75 kb SalI-BglII Fragment of Plasmid pKC203

About 5 μl. (5 μg.) of plasmid pKC203 (constructed in Example 1) in TE buffer (10 mM Tris-HCl, pH 8., 1 mM EDTA), 5 μl. DTT (100 mM Dithiothreitol), 5 μl. (1000 μg./ml.) BSA (bovine serum albumin), 25 μl. water, 5 μl. (5 units) BglII restriction enzyme and 5 μl. 10X reaction mix* were incubated at 37° C. for about 1 hour. The reaction was terminated by incubation at 70° C. for 5 minutes and then the reaction mixture was cooled on ice. Next, about 1.1 μl. of 5M NaCl, 4 μl. water and 5 μl. (5 units) SalI restriction enzyme were added followed by incubation at 37° C. for 1 hour. The reaction was terminated by incubation at 70° C. for 5 minutes and then the reaction mixture was cooled on ice, extracted with each of phenol and chloroform:isoamyl alcohol (24:1) and then ethanol precipitated. The desired ∼2.75 kb SalI-BglII restriction fragments were conventionally separated and isolated by agarose gel electrophoresis (Maniatis et al., 1982, Molecular Cloning, Cold Spring Harbor Laboratory, Cold Spring Harbor, N.Y.). The desired ∼2.75 kb fragments were then dissolved in about 20 μl. of TE buffer and stored at 0° C.

*Reaction mix (10X) for BglII restriction enzyme was prepared with the following composition:
600 mM NaCl
100 mM Tris-HCl, pH 7.4
100 mM MgCl₂

D. Ligation and Final Construction of *E. coli* K12 RR1/pKC222

About 5 μg. of plasmid pKC7, the construction of which is disclosed in Rao and Rogers, 1979, Gene 7:79, were treated with SalI and BglII restriction enzyme in substantial accordance with the procedure of Example 1C. After the enzymes were inactivated by heating at 70° C. for 5 minutes, about 1 μl. (1 μg.) of the DNA was mixed with about 1 μl. (1 μg.) of the ∼2.75 kb SalI-BglII fragment of plasmid pKC203, 37 μl. water, 5 μl. (10 mM) ATP, 5 μl. ligation mix* and 1 μl. T4 DNA Ligase (∼10⁵ New England Bio Lab. Units). The mixture was incubated at 16° C. for about 16 hours and then the reaction was terminated by incubation at 70° C. for 5 minutes. After cooling on ice, the resultant ligated mixture was used to transform, in substantial accordance with the transformation procedure of Wensink, 1974, *E. coli* K12 RR1 on TY plates containing 200 μg./ml. of antibiotic hygromycin B. Bacterial strain *E. coli* K12 RR1 has been deposited and made part of the stock culture collection of the Northern Regional Research Laboratory, Peoria, Ill., from which it is available to the public under the accession number NRRL B-15210.

*Ligation mix was prepared with the following composition:
500 mM Tris-HCl, pH 7.8
200 mM Dithiothreitol
100 mM MgCl₂

Figure 2:
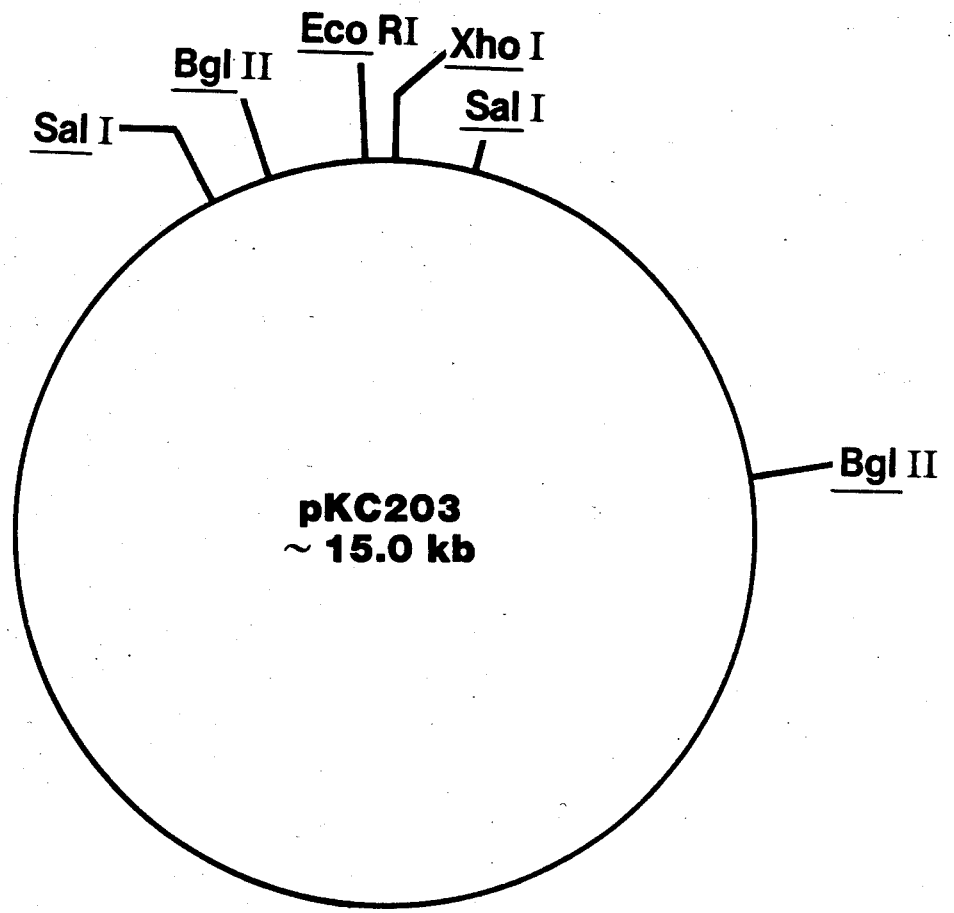

Some of the resultant transformants, as conventionally shown by agarose gel electrophoresis (Rao and Rogers, 1978) and other tests, contained only the desired ∼6.8 kb plasmid. Such a transformant, designated herein as *E. coli* K12 RR1/pKC222, was selected, plated on TY agar containing 200 μg./ml. of antibiotic hygromycin B and then cultered using conventional microbiological techniques. The resultant cells were used to isolate plasmid pKC222 in substantial accordance with the procedure of Example 1A. The presence of the antibiotic hygromycin B and G418 resistance genes in plasmid pKC222 was further confirmed by subsequent transformation, selection, restriction enzyme and sequence analysis. A restriction site and functional map of plasmid pKC222 is shown in FIG. 1 of the accompanying drawings.

EXAMPLE 2

Construction of Plasmid pTI104 and *E. coli* K12 RR1/pTI104

About 1.5 μl. (1 μg.) of plasmid pKC222, 0.5 μl. of 10X buffer (0.5M Tris, pH 7.5, 0.1M MgCl₂), 0.5 μl. each of (200 mM) dCTP, dATP, TTP and dGTP and 1 μl. (containing 1 unit of DNA polyermase I large (Klenow) fragment were incubated at 37° C. for 15 minutes. After heat inactivation of the polymerase, BamHI linkers* were added in substantial accordance with the procedure of Roberts and Lauer, 1979, Methods In Enzymology 68:473. The resultant BamHI linker-containing DNA was conventionally digested with BamHI restriction enzyme and then ligated in substantial accordance with the procedure of Example 1D. After digestion with SacI restriction enzyme to reduce the number of parental plasmids, the resultant plasmid pTI104 DNA was used to transform, in substantial accordance with the procedure of Wensink, 1974, *E. coli* K12 RR1. The transformed cells were plated on LB plates (Rosenberg and Court, 1979, Ann. Rev. Genet. 13:319) containing ampicillin at 50 µg./ml. The resultant ampicillin resistant *E. coli* K12 RR1/pTI104 cells were conventionally isolated and cultured for the subsequent production and isolation of plasmid pTI104. The structure of plasmid pTI104 was confirmed by transformation, selection, restriction enzyme and sequence analysis. A restriction site map of plasmid pTI104 is presented in FIG. 3 of the accompanying drawings.

*BamHI linkers [d(CCGGATCCGG)] can be obtained from the following source:
Collaborative Research
128 Spring Street
Lexington, Mass. 02173

EXAMPLE 3

Construction of Plasmid pTI106 and *E. coli* K12 JA221/pTI106

A. Construction of the ~0.17 kb PstI-BamHI Fragment of Plasmid pTI104

The desired construction was made in substantial accordance with the teaching of Example 1C except that plasmid pTI104 and PstI and BamHI restriction enzymes and PstI reaction mix*, rather than plasmid pKC203 and SalI and BglII restriction enzymes and BglII reaction mix, were used. The resultant ~0.17 kb PstI-BamHI fragments were dissolved in about 20 µl. of TE buffer and stored at 0° C.

*Reaction mix (10X) for PstI restriction enzyme was made with the following composition:
PstI Reaction Mix
600 mM NaCl
60 mM Tris-HCl, pH
60 mM MgCl$_2$ B. Construction of the ~9.3 kb PstI-BamHI Fragment of Plasmid pMC1403

1. Isolation of Plasmid pMC1403

Plasmid pMC1403 was isolated from *E. coli* K12 BE904/pMC1403 (NRRL B-15213). The strain was cultured and the plasmid was isolated in substantial accordance with the teaching of Example 1A.

Plasmid pMC1403 contains the lacZ gene with a BamHI site, at the triplet for amino acid 8, which is in the same translational reading frame as the ~0.17 kb PstI-BamHI fragment of plasmid pTI104. Therefore, PstI-BamHI digestion of plasmid pMC1403 results in a fragment which contains a portion of the lacZ structural gene but which lacks a DNA sequence for driving transcription and expression.

2. Construction of the ~9.3 kb PstI-BamHI Fragment of Plasmid pMC1403

The desired construction was made in substantial accordance with the teaching of Example 1C except that plasmid pMC1403 and PstI and BamHI restriction enzymes and PstI reaction mix, rather than plasmid pKC203 and SalI and BglII restriction enzymes and BglII reaction mix, were used. The resultant ~9.3 kb PstI-BamHI fragments were dissolved in about 20 µl. of TE buffer and stored at 0° C.

C. Ligation and Final Construction

About 2 µl. (1 µg.) of the ~0.17 kb PstI-BamHI fragment of plasmid pTI104 and about 2 µl. (1 µg.) of the ~9.3 kb PstI-BamHI fragment of plasmid pMC1403 were ligated and the resultant plasmid pTI106 transformed into *E. coli* K12 JA221 in substantial accordance with the ligation and transformation procedure of Example 2. Bacterial strain *E. coli* K12 JA221, deposited and made part of the permanent stock culture collection of the Northern Regional Research Laboratory, Peoria, Ill., from which it is available to the public under the accession number NRRL B-15211, is $R_k^-M_k^+$. Therefore, *E. coli* K12 JA221 is useful for modifying plasmid pTI106 so that subsequent transformation of *E. coli* K12 $R_k^+$ hosts such as, for example, *E. coli* K12 BE904, can be done.

EXAMPLE 4

Construction of *E. coli* K12 BE904/pTI106

A. Isolation of Plasmid pTI106 from *E. coli* K12 JA221/pTI106

Bacterial strain *E. coli* K12 JA221/pTI106 was cultured and plasmid pTI106 was isolated in substantial accordance with the teaching of Example 1A.

B. Transformation

Plasmid pTI106 was used to transform lacZ mutant *E. coli* K12 BE904, a strain deposited and made part of the permanent stock culture collection of the Northern Regional Research Laboratory, Peoria, Ill., from which it is available to the public under the accession number NRRL B-15212, in substantial accordance with the teaching of Example 2. The resultant transformants were selected on X-G plates (Miller, 1972, Experiments in Molecular Genetics, Cold Spring Harbor Laboratory, Cold Spring Harbor, N.Y.). The pTI106 transformants produced dark blue colonies on the X-G plates indicating that the DNA of the present invention, which comprises the ~0.17 kb PstI-BamHI fragment of plasmid pTI104 or pTI106, is functional and useful for directing the transcription and expression of structural genes. This was further confirmed by in vitro assay which showed the presence of β-galactosidase activity in the transformants.

EXAMPLE 5

Figure 4:
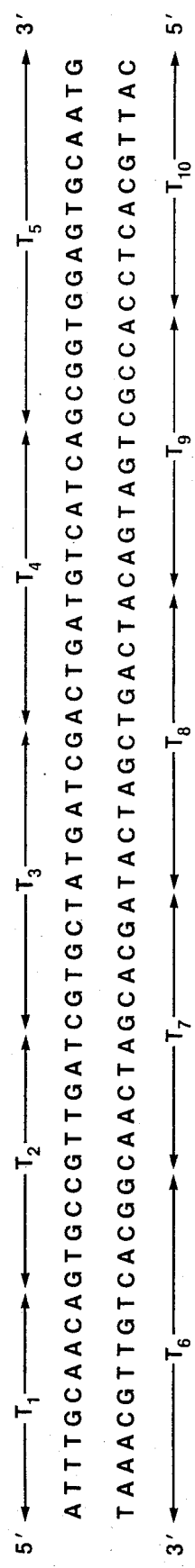

Synthetic Construction of the Polycistronic Apramycin (aac(3)IV) and Hygromycin B (aph(4)) Promoter and Shine-Dalgarno DNA Sequence with Translational-Start Triplet The desired construction involves the synthesis and subsequent ligation of the 10 oligonucleotides ($T_1$ through $T_{10}$) that are indicated by the double headed arrows in FIG. 4 of the accompanying drawings. Oligonucleotides $T_1$ to $T_{10}$ are synthesized by the modified phosphotriester method using fully protected trideoxyribonucleotide building blocks (Itakura et al., 1977 and Crea et al., 1978). The various oligodeoxyribonucleotides are shown in Table I.

TABLE 1

Synthetic Oligonucleotides for Apramycin (aac(3)IV)
and Hygromycin B (aph(4)) Promoter, Shine-Dalgarno
Sequence and Translational Start Triplet

| Compound | Sequence (5' → 3') | Length |
|---|---|---|
| T1 | A—T—T—T—G—C—A—A—C—A | 10 |
| T2 | G—T—G—C—C—G—T—T—G—A—T | 11 |
| T3 | C—G—T—G—C—T—A—T—G—A—T—C—G | 13 |
| T4 | A—C—T—G—A—T—G—T—C—A—T—C—A | 13 |
| T5 | G—C—G—G—T—G—G—A—G—T—G—C—A—A—T—G | 16 |
| T6 | G—G—C—A—C—T—G—T—T—G—C—A—A—A—T | 15 |
| T7 | A—G—C—A—C—G—A—T—C—A—A—C | 12 |
| T8 | A—T—C—A—G—T—C—G—A—T—C—A—A—T | 13 |
| T9 | A—C—C—G—C—T—G—A—T—G—A—C | 12 |
| T10 | C—A—T—T—G—C—A—C—T—C—C | 11 |

Figure 5:
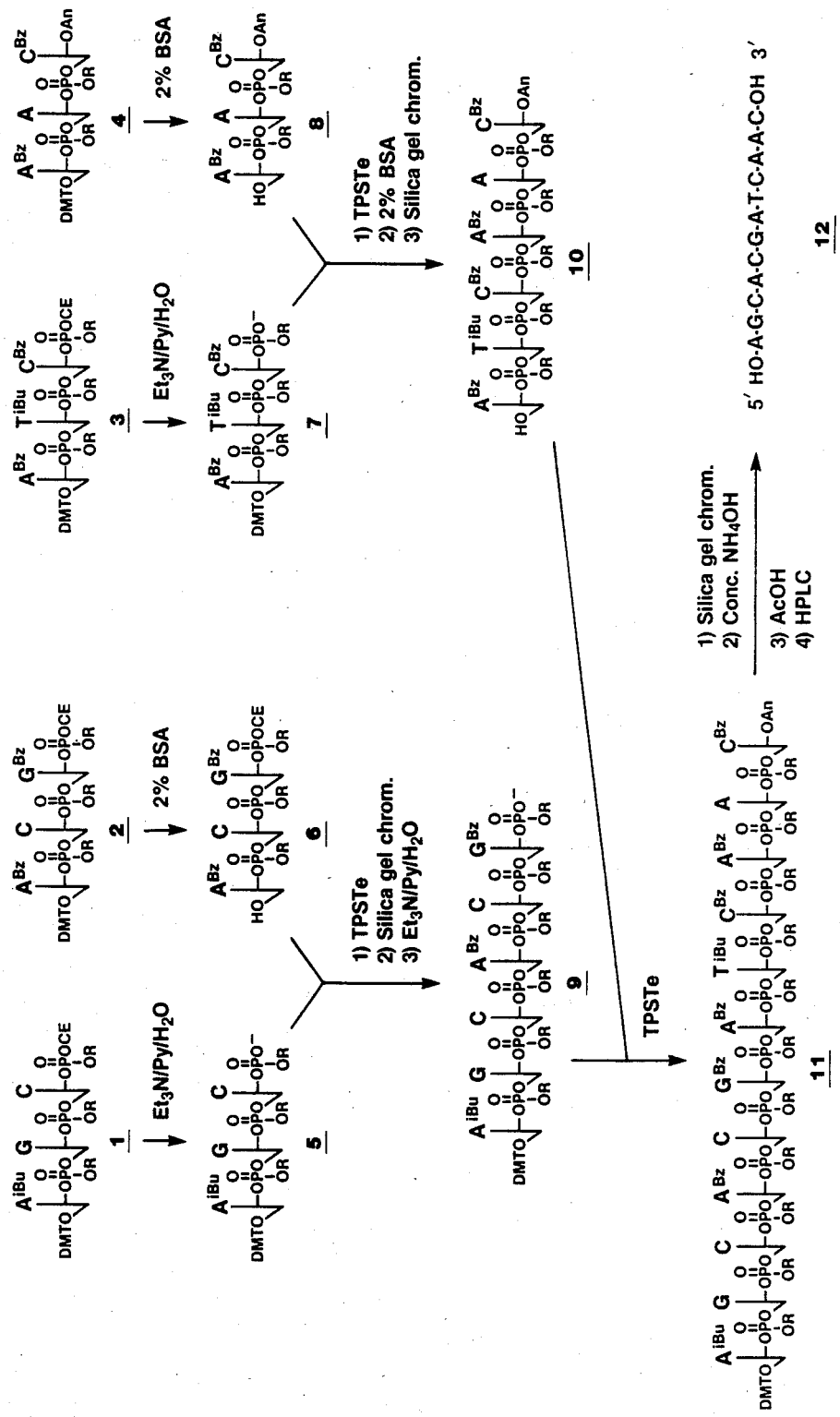

The above synthesis is typified by the following procedure for fragment T7 as summarized in FIG. 5 of the accompanying drawings. Various nucleotide fragments that are used in the synthesis of T7 are numerically designated in the Figure. The abbreviations employed are as follows: TPSTe, 2,4,6-triisopropylbenzenesulfonyltetrazole; BSA, benzene sulfonic acid; TLC, thin layer chromatography; HPLC, high performance liquid chromatography; DMT, 4,4'-dimethoxytrityl; CE, 2-cyanoethyl; R, p-chlorophenyl; Bz, benzoyl; An, anisoyl; iBu, isobutyryl; Py, pyridine; AcOH, acetic acid; Et$_3$N, triethylamine.

The fully protected trideoxyribonucleotides 4 (85 mg, 0.05 mmol) and 2 (180 mg, 0.1 mmol) are deblocked at the 5' hydroxyls by treatment with 2% BSA in 7:3 (v/v) chloroform/methanol (10 and 20 ml, respectively) for 10 minutes at 0° C. Reactions are stopped by addition of saturated aqueous ammonium bicarbonate (2 ml), extracted with chloroform (25 ml), and washed with water (2×10 ml). The organic layers are dried (magnesium sulfate), concentrated to small volumes (about 5 ml), and precipitated by addition of petroleum ether (35°-60° C. fraction). The colorless precipitates are collected by centrifugation and dried in a dessicator in vacuo to give 6 and 8, respectively, each homogeneous by silica gel tlc (Merck 60 F254, chloroform/methanol, 9:1).

Trimers 1 and 3 (270 mg, 0.15 mmol; 145 mg, 0.075 mmol) are converted into their phosphodiesters (5 and 7) by treatment with triethylamine/pyridine/water (1:3:1, v/v, 10 ml) for 25 minutes at ambient temperature. Reagents are removed by rotary evaporation and the residues dried by repeated evaporations with anhydrous pyridine (3×10 ml). Trimer 8 (0.05 mmol) and trimer 7 are combined with TPSTe (50 mg, 0.15 mmol) in anhydrous pyridine (3 ml) and the reaction mixture left in vacuo at ambient temperature for two hours. TLC analysis shows that 95% of the trimer 8 has been converted into hexamer product (visualized by detection of the DMT group by spraying with 10% aqueous sulfuric acid and heating at 60° C.). The reaction is quenched by addition of water (1.0 ml) and the solvent evaporated under reduced pressure. After removal of pyridine by coevaporations with toluene, the hexamer is deblocked at the 5' position with 2% BSA (8 ml) as described above for trimers 4 and 2. The product (10) is purified on a silica gel column (Merck 60 H, 3.5×5 cm) by step gradient elution with chloroform/methanol (98:2 to 95:5, v/v). Fractions containing product 10 are evaporated to dryness.

Similarly, trimer 5 is coupled to 6 and the fully protected product directly purified on silica gel. This latter compound is deblocked at the 3' end by triethylamine/pyridine/water as described above to give fragment 9.

Finally, hexamers 9 and 10 are coupled in anhydrous pyridine (2 ml) with TPSTe (75 mg, 0.225 mmol) as the condensing agent. Upon completion (4 hours, ambient temperature) the mixture is rotary evaporated and the residue chromatographed on silica gel. Product 11 (160 mg) is obtained by precipitation with petroleum ether and appears homogeneous on TLC. A portion of compound 11 (20 mg) in pyridine (0.5 ml) is completely deblocked by treatment with concentrated ammonium hydroxide (7 ml, 8 hours, 60° C.) and subsequent treatment in 80% acetic acid (15 minutes, ambient temperature). After evaporation of acetic acid, the solid residue is dissolved in 4% aqueous ammonium hydroxide (v/v, 4 ml) and extracted with ethyl ether (3×2 ml). The aqueous phase is concentrated to 1-2 ml and a portion applied to HPLC for purification of 12. The fractions corresponding to the major peak are pooled (ca. 2.0 O.D.$_{254}$ units) and concentrated to about 5 ml. The final product 12 is desalted on Bio-gel P-2 (1.5×100 cm) by elution with 20% aqueous ethanol, reduced to dryness and resuspended in water (200 µl) to give a solution of A$_{254}$=10. The sequence of 12 is confirmed by two-dimensional sequence analysis.

Figure 6:
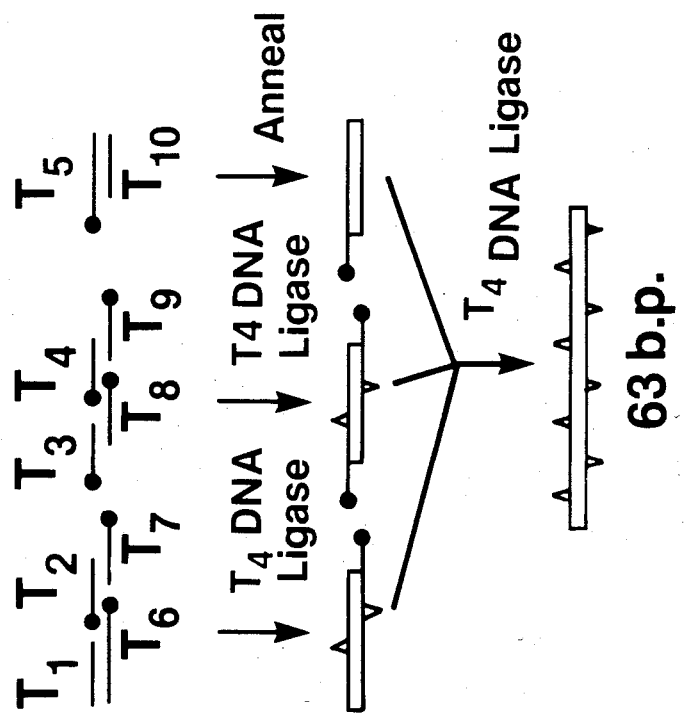

The desired synthetic DNA sequence is assembled from the 10 synthetic oligonucleotides by methods previously described in detail for somatostatin (Itakura et al., 1977), insulin (Goeddel et al., 1979), and growth hormone (Goeddel, Heyneker, et al., 1979, Nature 281:544). Ten microgram quantities of oligonucleotides T$_2$ through T$_9$ are quantitatively phosphorylated with [γ-$^{32}$P]-ATP (New England Nuclear) in the presence of T$_4$ polynucleotide kinase (Goeddel et al., 1979), to give specific activities of approximately 1 Ci/mmol. Radiolabelled fragments are purified by 20% polyacrylamide/7M urea gel electrophoresis and sequences of the eluted fragments are verified by two-dimensional electrophoresis/homochromatography (Jay et al., 1974, Nucleic Acids Res. 1:331) of partial snake venom digests. Fragments T$_1$ and T$_{10}$ are left unphosphorylated to minimize undesired polymerization during subsequent ligation reactions. These oligonucleotides (2 µg each) are assembled in three groups of fragments (see FIG. 6 of the accompanying drawings), by T$_4$ DNA ligase using published procedures (Goeddel et al., 1979). The reaction products are purified by gel electrophoresis on a 15% polyacrylamide gel containing 7M urea (Maxam and Gilbert, 1977, Proc. Nat. Acad. Sci. USA 71:3455). The isolated products are ligated together and the reaction mixture resolved by 10% polyacrylamide gel electrophoresis. DNA in the size range of the desired fragment (60-70 base pairs) is electroeluted.

The thus constructed synthetic apramycin (aac(-3)IV)-hydromycin B (aph(4)) promoter, Shine-Dalgarno sequence and translational-start triplet can be blunt end ligated, in substantial accordance with the procedure of Maniatis et al, 1982, to any gene that encodes a functional polypeptide. Such genes, including, for example, genes encoding human preproinsulin, human proinsulin, human insulin A-chain, human insulin B-chain, human growth hormone, bovine growth hormone and human interferon, are known and also can be synthesized and appropriately modified using literature procedures analogous to those disclosed herein above. Thus, the DNA of the present invention can be used to drive the transcription and expression of any structural gene for production of either heterologous or fused gene products.

I claim:

1. A constructed DNA consisting essentially of the promoter, Shine-Dalgarno sequence, and translational start triplet of the polycistronic apramycin (aac(3)IV) and hygromycin (aph(4)) resistance genes.

2. A constructed DNA which comprises the sequence

```
5'-ATTTGCAACAGTGCCGTTGATCGTGCTATGA
   ||||||||||||||||||||||||||||||||
3'-TAAACGTTGTCACGGCAACTAGCACGATACT

TCGACTGATGTCATCAGCGGTGGAGTGCAATG—3'
||||||||||||||||||||||||||||||||
AGCTGACTACAGTAGTCGCCACCTCACGTTAC—5'
``` wherein
A is deoxyadenyl,
G is deoxyguanyl,
C is deoxycytosyl and
T is thymidyl.

3. A recombinant DNA cloning vector which comprises the sequence

```
5'-ATTTGCAACAGTGCCGTTGATCGTGCTATGA
   ||||||||||||||||||||||||||||||||
3'-TAAACGTTGTCACGGCAACTAGCACGATACT

TCGACTGATGTCATCAGCGGTGGAGTGCAATG    -3'
||||||||||||||||||||||||||||||||  —R
AGCTGACTACAGTAGTCGCCACCTCACGTTAC    -5'
``` wherein
A is deoxyadenyl,
G is deoxyguanyl,
C is deoxycytosyl,
T is thymidyl, and
R is a structural gene, exclusive of the translational start triplet, that codes for a functional polypeptide that is heterologous with respect to E. coli.

4. The recombinant DNA cloning vector of claim 3 which is a plasmid.

5. A DNA restriction fragment which is selected from the group consisting of the ~0.17 kb PstI-SacI fragment of plasmid pKC222, ~0.17 kb PstI-BamHI fragment of plasmid pTI104, and the ~0.17 kb PstI-BamHI fragment of plasmid pTI106.

6. The plasmid of claim 4 in which the structural gene is selected from the group consisting of genes that code for β-galactosidase, human pre-proinsulin, human proinsulin, human insulin A-chain, human insulin β-chain, non-human insulin, human growth hormone, non-human growth hormone, bovine growth hormone, human interferon, non-human interferon, viral antigen, and urokinase.

7. The plasmid of claim 6 in which the structural gene codes for β-galactosidase.

8. The plasmid of claim 6 in which the structural gene codes for human proinsulin.

9. The plasmid of claim 6 in which the structural gene codes for human insulin A-chain.

10. The plasmid of claim 6 in which the structural gene codes for human growth hormone.

11. The plasmid of claim 6 in which the structural gene codes for bovine growth hormone.

12. The plasmid of claim 6 in which the structural gene codes for human insulin β-chain.

13. The plasmid of claim 6 which is selected from the group consisting of plasmid pTI104 and pTI106.

14. A bacterial host cell which is transformed by a recombinant DNA cloning vector which comprises

```
5'-ATTTGCAACAGTGCCGTTGATCGTGCTATGA
   ||||||||||||||||||||||||||||||||
3'-TAAACGTTGTCACGGCAACTAGCACGATACT

TCGACTGATGTCATCAGCGGTGGAGTGCAATG    -3'
||||||||||||||||||||||||||||||||  —R
AGCTGACTACAGTAGTCGCCACCTCACGTTAC    -5'
``` wherein
A is deoxyadenyl,
G is deoxyguanyl,
C is deoxycytosyl,
T is thymidyl, and
R is a structural gene, exclusive of the translational start triplet, that codes for a functional polypeptide that is heterologous with respect to E. coli.

15. The host cell of claim 14 in which the recombinant DNA cloning vector is a plasmid.

16. The host cell of claim 14 which is E. coli.

17. The host cell of claim 16 which is selected from the group consisting of E. coli K12 RR1/pTI104, E. coli K12 RR1/PTI106, E. coli K12 JA221/pTI106, E. coli K12 JA221/pTI104, E. coli K12 HB101/pTI104, E. coli K12 HB101/pTI106 and E. coli K12 BE904/pTI106.

18. The host cell of claim 15 which is a Streptomyces cell.

* * * * *